(12) United States Patent
D'Ascenzi

(10) Patent No.: US 8,663,994 B2
(45) Date of Patent: Mar. 4, 2014

(54) ANALYSIS OF MANNOSAMINE-CONTAINING CAPSULAR SACCHARIDES

(75) Inventor: Sandro D'Ascenzi, Siena (IT)

(73) Assignee: Novartis AG, Basel (CH)

( * ) Notice: Subject to any disclaimer, the term of this patent is extended or adjusted under 35 U.S.C. 154(b) by 236 days.

(21) Appl. No.: 12/308,830

(22) PCT Filed: Jun. 27, 2007

(86) PCT No.: PCT/IB2007/002821
§ 371 (c)(1),
(2), (4) Date: Jul. 2, 2009

(87) PCT Pub. No.: WO2008/001222
PCT Pub. Date: Jan. 3, 2008

(65) Prior Publication Data
US 2010/0022015 A1   Jan. 28, 2010

(30) Foreign Application Priority Data
Jun. 28, 2006  (GB) .................................. 0612854.0

(51) Int. Cl.
*G01N 33/15* (2006.01)
(52) U.S. Cl.
USPC .............................. 436/94; 436/91; 436/161
(58) Field of Classification Search
USPC ........................ 436/91, 93, 96, 106
See application file for complete search history.

(56) References Cited

U.S. PATENT DOCUMENTS 4,206,200 A * 6/1980 Guthohrlein et al. ...... 424/250.1
4,246,349 A   1/1981 Messing et al.
6,290,967 B1 * 9/2001 Volkin et al. ............... 424/204.1

FOREIGN PATENT DOCUMENTS

WO   WO 2005/090985   9/2005
WO   WO-2005/090986   9/2005

OTHER PUBLICATIONS

Bach, et al. "An Expert System from High Performance Liquid Chromatography Methods Development." Chapter 22 of Artificial Intelligence Applications in Chemistry a volume of ACS Symposium Series, American Chemical Society, Washington DC, 1986.*
Yokota, Hiroyuki et al. "Monosaccharide composition analysis of pamiteplase by anion exchange chromatography with pulsed amperometric detection." Journal of Pharmaceutical and Biomedical Analysis (1999) 21 767-774.*
Ricci, S. et al. "Development of a new method for the quantitative analysis of the extracellular polysaccharide of *Neisseria meningitidis*. . . " Vaccine, 19:1989-1997 (2001).
Bardotti, A. et al. "Quantitative determination of saccharide in Haemophilus influenzae type b glycoconjugate vaccines, alone and in . . . " Vaccine 18(19): 1982-1993 (2000).

* cited by examiner

*Primary Examiner* — Christopher A Hixson
(74) *Attorney, Agent, or Firm* — Helen Lee; Otis Littlefield

(57) ABSTRACT

Analysis of compositions that include saccharides having mannosamine residues, such as the capsular saccharide of *N. meningitidis* serogroup A, is facilitated by a method comprising the steps of: (i) hydrolysing polysaccharide in the sample, to give a hydrolysate; (ii) subjecting the hydrolysate to liquid chromatography; and (iii) detecting any mannosamine-6-phosphate separated in step (ii).

25 Claims, 3 Drawing Sheets

ANALYSIS OF MANNOSAMINE-CONTAINING CAPSULAR SACCHARIDES

All documents cited herein are incorporated by reference in their entirety.

RELATED APPLICATIONS

This application is the U.S. National Phase of International Application No. PCT/IB2007/002821, filed Jun. 27, 2007 and published in English, which claims priority to Great Britain Application No. 0612854.0, filed Jun. 28, 2006. The teachings of the above applications are incorporated herein in their entirety by reference.

TECHNICAL FIELD

This invention concerns the analysis and quality control of compositions that include saccharides having mannosamine residues, such as the capsular saccharide of *N. meningitidis* serogroup A.

BACKGROUND OF THE INVENTION

The capsular saccharide of serogroup A *Neisseria meningitidis* (MenA) is a homopolymer of α(1-6)-linked N-acetyl-mannosamine-6-phosphate. It is included as an immunogen in vaccines, either as free saccharide or conjugated to a carrier protein.

The European Pharmacopoeia recommends that quantitative determination of the MenA saccharide should be based on calorimetric determination of its phosphorus. Reference 1 discloses an alternative method for the quantitative determination of MenA saccharide by: trifluoracetic acid (TFA) hydrolysis (2 M at 80° C. for 3 h); followed by chromatographic separation and quantification of the liberated mannosamine-6-phosphate from the area of the peak obtained using an IonPac AS11 column coupled to the sensitive pulsed amperometric detector ED40. The highly selective nature of this method circumvents interference problems associated with the calorimetric phosphorus assay.

The MenA saccharide may be lyophilised, in which case stabilisers such as sucrose may be combined with the MenA saccharide. Such stabilisers will be present at much higher levels than the MenA saccharide itself Sucrose can interfere with the analysis of mannosamine-6-phosphate monosaccharides. Thus there is a need for an assay method for MenA that can function against a background of lyophilisation stabilisers such as sucrose.

DISCLOSURE OF THE INVENTION

The invention provides a method for assaying a sample suspected to contain a capsular saccharide from serogroup A *Neisseria meningitidis* ('MenA-CPS'), comprising the steps of: (i) hydrolysing any MenA-CPS in the sample, to give a hydrolysate; (ii) subjecting the hydrolysate to liquid chromatography; and (iii) detecting any mannosamine-6-phosphate separated in step (ii).

The Sample

The sample is suspected to contain a capsular saccharide from serogroup A *Neisseria meningitidis* ('MenA-CPS'). Typical samples will be vaccines.

The sample may contain free (unconjugated) MerA-CPS and/or conjugated MenA-CPS. Thus the method may be used to assay CPS prepared from a bacterium, CPS after purification, CPS prior to conjugation, and/or CPS after conjugation.

In a sample containing conjugated MenA-CPS, a comparison of levels of free CPS to the total CPS in a sample (i.e. the ratio of unconjugated CPS:(unconjugated+conjugated) CPS) can be used to determine stability. High levels of unconjugated CPS are undesirable. A time-series of such assays can reveal if a conjugate is stable e.g. during storage.

The level of free CPS can also be used to check if a conjugation reaction has gone to completion.

The sample will typically be aqueous, but may have been reconstituted into aqueous form from a dried form e.g. from a lyophilisate. Thus the sample may contain lyophilisation stabilizers. These stabilizers include substances such as sugar alcohols (e.g. mannitol, etc.), disaccharides (e.g. sucrose, trehalose, etc.), and other simple saccharides. An advantage of the methods of the invention is that they can assay MenA-CPS against a background of sucrose, without requiring any pre-separation of the MenA-CPS and the sucrose.

The sample may be diluted prior to analysis. After analysis, the level of saccharide in the sample can then be related to the level in the original undiluted material. Dilution is useful, for example, to ensure that analysis of a sample gives a result within a desired portion of a calibration curve.

The sample may comprise polysaccharides (e.g. with a degree of polymerisation of at least 10, e.g. 20, 30, 40, 50, 60 or more), oligosaccharides (e.g. with a degree of polymerisation of from 2 to 10), or monosaccharides. Oligosaccharides and monosaccharides may be the result of depolymerisation and/or hydrolysis of a parent polysaccharide e.g. the analyte may be a saccharide-containing fragment of a larger saccharide. The sample will typically contain saccharides of a size that is sufficient to function as antigens in humans.

In addition to MenA-CPS, the sample may contain other bacterial capsular saccharides (including those that do not contain mannosamine residues) e.g. from *Haemophilus influenzae* type B, from other meningococcal serogroups (e.g. C, W135 and/or Y), from *Streptococcus pneumoniae*, etc.

Samples may also include other components, such as non-antigen components often found in vaccines. For example, these may include carriers, adjuvants, excipients, buffers, etc., as described in more detail below.

Samples may include one or more pharmaceutical carrier(s) and/or excipient(s). Sterile pyrogen-free, phosphate-buffered physiologic saline is a typical carrier. A thorough discussion of pharmaceutically acceptable excipients is available in reference 2.

To control tonicity, samples may include a physiological salt, such as a sodium salt. Sodium chloride (NaCl) is one such salt, which may be present at between 1 and 20 mg/ml.

Samples may have an osmolality of between 200 mOsm/kg and 400 mOsm/kg e.g. between 240-360 mOsm/kg, or within the range of 290-320 mOsm/kg.

Samples may include one or more buffers. Typical buffers include: a phosphate buffer; a Tris buffer; a borate buffer; a succinate buffer; a histidine buffer; or a citrate buffer. Buffers will typically be included in the 5-20 mM range. Such buffers may be included in the aqueous and/or lyophilised components.

Samples may have a pH between 5.0 and 7.5, and more typically between 5.0-6.0 or between 6.0-7.0.

Samples may be sterile.

Samples may be non-pyrogenic e.g. containing <1 EU (endotoxin unit, a standard measure) per ml Samples may be gluten free.

Samples may be unadjuvanted, or they may include adjuvant, such as an aluminium salt.

Samples may include a preservative, such as 2-phenoxyethanol.

In some situations, it is useful to spike the sample with a known amount of the analyte in question e.g. to add a known quantity of serogroup A saccharide, either in conjugated or unconjugated form. Spiking studies can be useful for calibration, and for studying sensitivity, variability, recovery, etc.

Hydrolysis

The methods of the invention involve hydrolysis of the MenA-CPS. Typical hydrolysis methods involve acid hydrolysis e.g. using trifluoroacetic acid (TFA). Treatment with 2M TFA for 2 hours at 100° C. is typically suitable for total hydrolysis.

Total MenA-CPS can be prepared from a sample including conjugated MenA-CPS by subjecting the whole sample to hydrolysis, as described below. If measurement of only conjugated or unconjugated MenA-CPS is desired, however, then conjugated and unconjugated MenA-CPS should be separated from each other prior to hydrolysis. Suitable separation techniques include selective precipitation, size-based methods, solid-phase extraction [3], etc.

Anion Exchange Chromatography

The results of MenA-CPS hydrolysis can be analysed by liquid chromatography. Thus the methods of the invention will typically utilize a liquid chromatography column, and will involve analysing the output of such a column.

Various liquid chromatography columns can be used, but it the invention will typically be used with high performance liquid chromatography (HPLC). The invention is particularly useful for analysing the results of separation by high performance anion exchange chromatography (HPAEC) or by high performance cation exchange chromatography (HPCEC). HPAEC is a common technique used for saccharide characterisation, often in combination with pulsed amperometric detection (PAD) [4,5]. Suitable HPAEC-PAD systems are provided by Dionex™ Corporation (Sunnyvale, Calif.) e.g. the BioLC™ system. In these systems, the eluate from a HPAEC column is analysed using PAD i.e. based on electrical current. At suitable (high) pH, carbohydrates can be electrocatalytically oxidised at the surface of electrodes by applying a positive potential. The current generated is this way is proportional to the carbohydrate concentration, allowing detection and quantification of the carbohydrate by amperometry. Compared with simple amperometric detection, PAD intersperses short pulses of a cleaning and regeneration potential with the standard detecting potential, thereby avoiding difficulties that arise when oxidation products of analytes foul the electrodes.

Non-amperometric methods can be combined with PAD for analyzing eluates e.g. see ref. 6.

Thus the hydrolysed MenA-CPS can be subjected to HPAEC for separation and the separated materials can be detected by PAD. As shown in the examples below, HPAEC-PAD can separate hydrolysed mannosamine-phosphate residues from other background materials in a sample, including excess sucrose.

Preferred columns are those that spontaneously retain saccharides such that they have to be eluted from the column. Elution from the chromatography column can be an isocratic elution or a gradient elution. Eluents including hydroxide and/or acetate salts are typical eluents used during HPAEC-PAD analysis of saccharides. It is also possible, however, to use anions such as nitrate, chloride, etc. Sodium salts are typically used. For eluting analytes from AEC columns then the eluent will generally be basic e.g. the pH will be >8, >9, >10, >11, >12, >13, etc. Hydroxide salts (e.g. NaOH) can be used to achieve the desired pH.

Eluates may be subjected to chemical suppression of hydroxide ions, particularly where the ions interfere with an analytical detection technique that is being used. A micromembrane suppressor can conveniently be used, such as the MMS products from Dionex™. The 'MMS III' product uses continuous chemical suppression to enhance analyte conductivities while decreasing eluent conductivity, and enables direct conductivity detection with ion-exchange applications using isocratic or gradient elution over wide concentration ranges.

Suitable HPAEC columns for use with the invention are the "CarboPac" columns marketed by Dionex, such as the PA1 [10 µm diameter polystyrene substrate 2% crosslinked with divinylbenzene, agglomerated with 500 nm MicroBead quaternary ammonium functionalized latex (5% crosslinked)], PA100, PA20, PA10 [10 µm diameter ethylvinylbenzene substrate 55% crosslinked with divinylbenzene, agglomerated with 460 nm MicroBead difunctional quaternary ammonium ion (5% crosslinked)], PA200 or MA1 columns.

Analytical HPAEC columns can be used in conjunction with pre-columns and/or trap columns. For instance, a PA10 analytical column can be used in conjunction with an inline PA10 guard column, and/or an inline trap (pre-treatment) column. Such columns can remove materials that would otherwise interfere with analyses e.g. an "AminoTrap" column can remove amino acids prior to saccharide analysis. Borate traps can also be used. TYPICAL "AminoTrap" resin has a 10 µm diameter substrate (ethylvinylbenzene 55% crosslinked with divinylbenzene) grafted with difunctional quaternary ammonium anion exchange sites, whereas a typical "BorateTrap" has a 20 µm diameter high capacity resin with very high selectivity for borate.

The PA1 and PA10 columns are both anion-exchange columns designed to be used with PAD to deliver high resolution separations of mono- and disaccharides, and the resins in both are 10 µm diameter nonporous beads covered with a fine latex of functionalized MicroBeads. Their pellicular resin structure permits excellent mass transfer, resulting in high resolution chromatography and rapid re-equilibration. Whereas PA1 is an all-purpose column suitable for determining monosaccharides and disaccharides in a variety of matrices, and is the column of choice for high resolution separations of linear polysaccharides, PA10 is optimized to determine the amino, neutral, and acidic monosaccharides that are found in the carbohydrate moieties of mammalian glycoproteins. The main difference between the PA1 and PA10 columns is that the resin in PA1 is polystyrene 2% crosslinked with divinylbenzene, but in PA10 it is ethylvinylbenzene 55% crosslinked with divinylbenzene.

To date, the most preferred HPAEC separation method for MenA-CPS involves a CarboPac PA10 column (4×250 mm) combined with a Guard PA10 pre-column (4×50 mm) and an AminoTrap column (4×50 mm).

After elution and detection, the invention may include the further step of determining a characteristic of a MenA-CPS analyte e.g. its DP (typically an average DP), its molecular weight, its purity, etc.

MenA-CPS

MenA-CPS $\{\rightarrow 6)$-D-ManpNAc(3/4OAc)-$\alpha$-$(1\rightarrow OPO_3\rightarrow\}$ is composed of N-acetylmannosamine residues linked together by $\alpha$-1-6 phosphodiester bonds. There is variable O-acetylation at the 3- and 4-positions on the saccharide ring. MenA-CPS can be represented as follows:

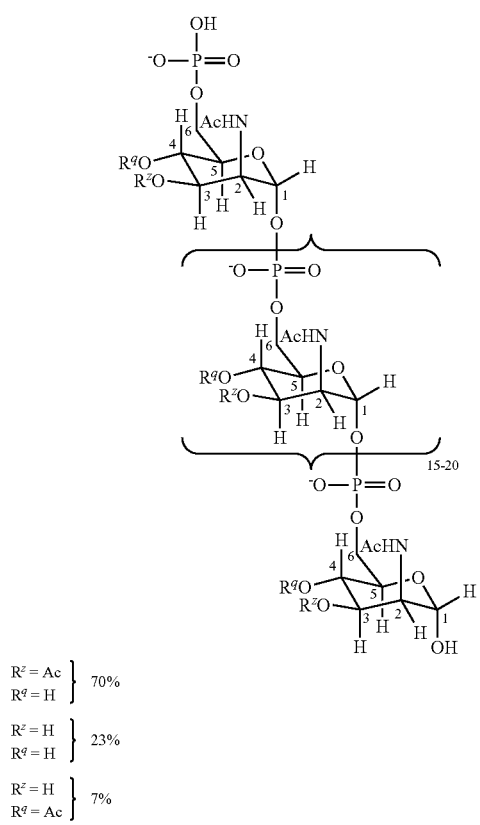

Reference 7 reports that the —OAc groups on the saccharide ring are important for the saccharide's immunogenicity.

As well as being used with native MenA-CPS, the invention can also be used with modified forms thereof, including de-O-acetylated forms, de-N-acetylated forms, substituted forms (e.g. see ref 8), etc. All of these derivatives are encompassed within the term "MenA-CPS", provided that they can still be separated and analysed by the methods of the invention. These MenA-CPS molecules may be prepared by purification from bacteria or, in whole or in part, by synthetic means [9].

The invention may also be used with capsular saccharides from other bacteria, provided that they include mannosamine or mannoseaminouronic acid residues, with optional acetylation and/or phosphorylation. These saccharides include: various *Streptococcus pneumoniae* types, such as IX, 19, 19A, 19F, and 57; *Bacteroides fragilis*; various Bacilli, including *B. pumilis, B. megaterium, B. subtilis* and *B. polymyxa*; some Staphylococci, including various *S. aureus* strains e.g. serotypes 5 and 8; etc. Thus samples may be suspected to contain a capsular saccharide from these bacteria.

Conjugates

The invention will typically be used to analyse saccharides that have been conjugated to carriers. Useful carrier proteins for covalent conjugation are bacterial toxins or toxoids, such as diphtheria toxoid or tetanus toxoid, or derivatives thereof such as the CRM197 diphtheria toxin mutant [10-12]. Other suitable carrier proteins include the *N. meningitidis* outer membrane protein [13], synthetic peptides [14,15], heat shock proteins [16,17], pertussis proteins [18,19], cytokines [20], lymphokines [20], hormones [20], growth factors [20], artificial proteins comprising multiple human CD4+ T cell epitopes from various pathogen-derived antigens [21] such as N19 [22], protein D from *H. influenzae* [23-25], pneumolysin [26], pneumococcal surface protein PspA [27], iron-uptake proteins [28], toxin A or B from *C. difficile* [29], etc.

Saccharides may be conjugated directly to the carriers, or via a linker. Direct linkages to the protein may comprise e.g. oxidation of the polysaccharide followed by reductive amination with the protein, as described in, for example, references 30 and 31. One type of linker-based conjugation involves reductive amination of the polysaccharide, coupling the resulting amino group with one end of an adipic acid linker group, and then coupling a protein to the other end of the adipic acid linker group [32,33]. Other linkers include O-propionamido [34], nitrophenyl-ethylamine [35], haloacyl halides [36], glycosidic linkages [37], 6-aminocaproic acid [38], ADH [39], $C_4$ to $C_{12}$ moieties [40] etc. Carbodiimide condenation can also be used [41].

General

The term "comprising" encompasses "including" as well as "consisting" e.g. a composition "comprising" X may consist exclusively of X or may include something additional e.g. X+Y.

The word "substantially" does not exclude "completely" e.g. a composition which is "substantially free" from Y may be completely free from Y. Where necessary, the word "substantially" may be omitted from the definition of the invention.

The term "about" in relation to a numerical value x means, for example, x±10%.

The methods of the invention can be used for analytical and/or preparative purposes. References to "analysing", "analysis", etc. should not be construed as excluding preparative methods.

The degree of polymerisation (DP) of a saccharide is defined as the number of repeating units in that saccharide. For a homopolymer, the SP is thus the same as the number of monosaccharide units. For a heteropolymer, however, the SP is the number of monosaccharide units in the whole chain divided by the number of monosaccharide units in the minimum repeating unit e.g. the DP of $(Glc-Gal)_{10}$ is 10 rather than 20, and the DP of $(Glc-Gal-Neu)_{10}$ is 10 rather than 30.

It will be appreciated that ionisable groups may exist in the neutral form shown in formulae herein, or may exist in charged form e.g. depending on pH. Although a phosphate group may be shown as —P—O—(OH)$_2$, this formula is merely representative of the neutral phosphate group, and other charged forms are encompassed by the invention. Similarly, references herein to cationic and anionic groups should be taken to refer to the charge that is present on that group under physiological conditions e.g. where an amine —NH$_2$ is protonated to give the cationic —NH$^{3+}$ group, this protonation is one that occurs at physiological pH. In addition where a carboxyl —COOH is deprotonated to give the anionic —COO$^-$ group, this protonation is one that can occur at physiological pH. Moreover, the invention encompasses salts of the charged forms of molecules of the invention. Sugar rings can exist in open and closed form and, while closed forms are shown in structural formulae herein, open forms are also encompassed by the invention. Similarly, the invention encompasses isomeric forms of the molecules of the invention, including tautomers (e.g. imine/enamine tautomers), conformers, enantiomers, diastereoisomers, etc.

MODES FOR CARRYING OUT THE INVENTION

Figure 1A:
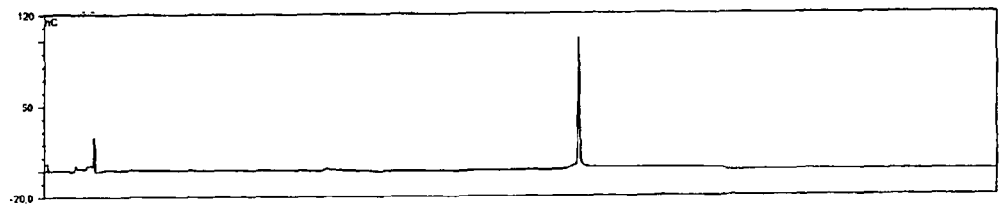
In FIG. 1A the analyte is retained; in 1B is it starting to elute; in 1C it is separated.
Figure 1B:
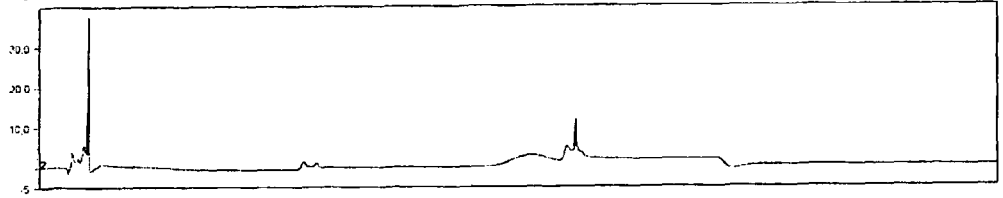
FIG. 1 shows the output of three HPAEC-PAD experiments. Elutions were isocratic with (A) 80 mM, (B) 90 mM or (C) 100 mM sodium acetate.

An analyte of interest is a MenA glycoconjugate that had been lyophilized using sucrose as a stabilizer. Compared to the amount of MenA saccharide (μg), the sucrose levels were very high (mg). An early analytical method separated sucrose from the MenA saccharide by 1 k ultrafiltration, but saccharide recoveries were not always consistent. In the method of the invention, the MenA saccharide is instead assayed as follows: TFA hydrolysis; inject onto PA10 CarboPac column; separate and detect by HPAEC-PAD. This method detects total MenA saccharide; if only unconjugated material is to be detected then solid phase extraction can first be used to remove conjugated MenA. Compared to the previous method, it avoids the slowness and inconsistency of pre-ultrafiltration. It also avoids the need for neutralization of the MenA sample after acid hydrolysis.

The most preferred HPAEC-PAD method is as follows. The Dionex chromatography system was equipped with a CarboPac PA10 analytical column (4×250 mm) in combination with a CarboPac PA10 guard column (4×50 mm) and a AminoTrap Trap columns (4×50 mm). Separation is performed with a flow rate of 1 ml/min using a gradient elution as follows: eluent A was NaOH 100 mM and eluent B was NaOH 100 mM 1M containing sodium acetate; applied with a starting isocratic elution at 8% B over 20 minutes to promote the separation of the sucrose and other interferences from mannosamine-6-P peak; a subsequent gradient elution from 8% B to 30% B over 20 minutes to separate the mannosamine-6-P peak. A triple-potential waveform was applied using the following settings: E1=0.05V, t1=0.4 s; E2=0.75V, t2=0.2 s; E3=−0.15V, t3=0.4 s.

Calibration

Conjugate samples with known MenA-CPS concentrations were obtained (ST). The conjugates had a CRM197 carrier protein. Solutions of unconjugated MenA-CPS were also obtained at five known concentrations.

ST and MenA-CPS samples (and a water blank) were hydrolyzed with TFA 2M at 100° C. for 2 hours. After hydrolysis, the acid samples were taken to 2-8° C. and filtered at 0.45 μm. Chromatographic analysis was performed using the Dionex DX500-GP40/GP50 chromatography systems. The systems were equipped with a Dionex CarboPac PA10 Analytical 4×250 mm columns in series with a CarboPac PA10 guard 4×50 mm and AminoTrap Trap columns 4×50 mm. The separation was performed with a flow rate of 1.0 ml/min, 20 μl of injection volume, using a gradient elution with NaOH 100 mM and $CH_3COONa$ 1M/NaOH 100 mM, according to the following settings:

| Time (min.) | Eluents |
|---|---|
| 0.00 | NaOH 100 mM = 92% |
| | $CH_3COONa$ 1M/NaOH 100 mM = 8% |
| 20.00 | NaOH 100 mM = 92% |
| | $CH_3COONa$ 1M/NaOH 100 mM = 8% |
| 20.01 | NaOH 100 mM = 92% |
| | $CH_3COONa$ 1M/NaOH 100 mM = 8% |
| 40.00 | NaOH 100 mM = 70% |
| | $CH_3COONa$ 1M/NaOH 100 mM = 30% |
| 40.01 | NaOH 100 mM = 92% |
| | $CH_3COONa$ 1M/NaOH 100 mM = 8% |
| 50.00 | NaOH 100 mM = 92% |
| | $CH_3COONa$ 1M/NaOH 100 mM = 8% |

A triple-potential waveform was applied using the following settings:

| Time (s) | Potential (V) | Integration |
|---|---|---|
| 0.00 | 0.05 | |
| 0.20 | 0.05 | Begin |
| 0.40 | 0.05 | End |
| 0.41 | 0.75 | |
| 0.60 | 0.75 | |
| 0.61 | −0.15 | |
| 1.00 | −0.15 | |

The resulting chromatography data were integrated and processed using Chromeleon Dionex Corporation, Version 6.50 SP3 Build 980.

Figure 1C:
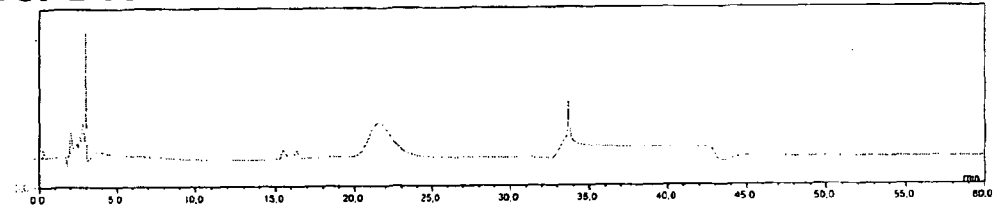

To optimize separation and determine the retention time of mannosamine-6-phosphate, isocratic elution conditions with sodium acetate (various concentrations, including 80 mM, 90 mM and 100 mM) were used. With the 80 mM elution the Man-6-P was retained (FIG. 1A); with the 100 mM elution it was separated (FIG. 1C).

Figure 2A:
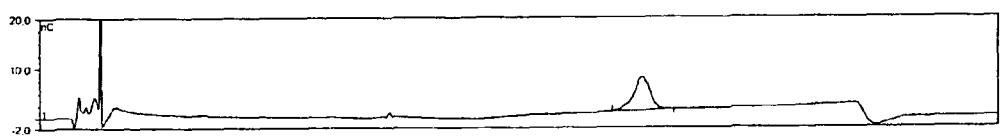
FIG. 2A shows a M6P standard; 2B shows total saccharide in a conjugated MenA-CPS sample; 2C shows free saccharide in a conjugated MenA-CPS sample.
Figure 2B:
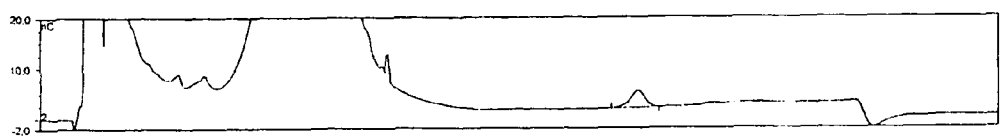
FIG. 2 also shows HPAEC-PAD results. Isocratic elution with 80 mM sodium acetate was used.
Figure 2C:
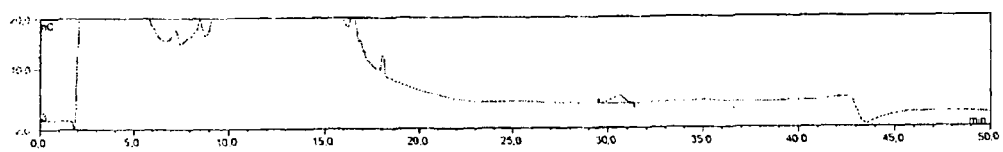
Figure 3:
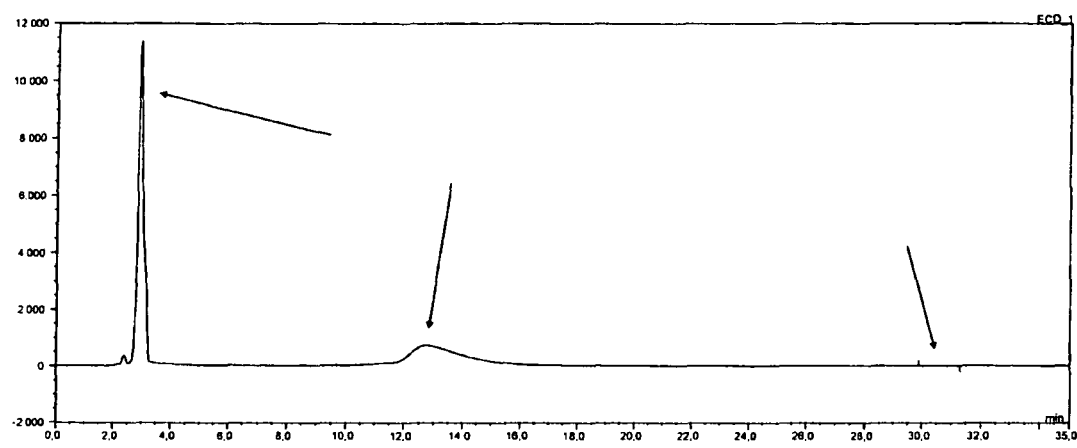
FIGS. 3 and 4 also show analysis of free saccharide. The three arrows in FIG. 3 are, from left to right, hydrolysed sucrose, matrix impurities and mannosamine-6-phosphate.
Figure 4:
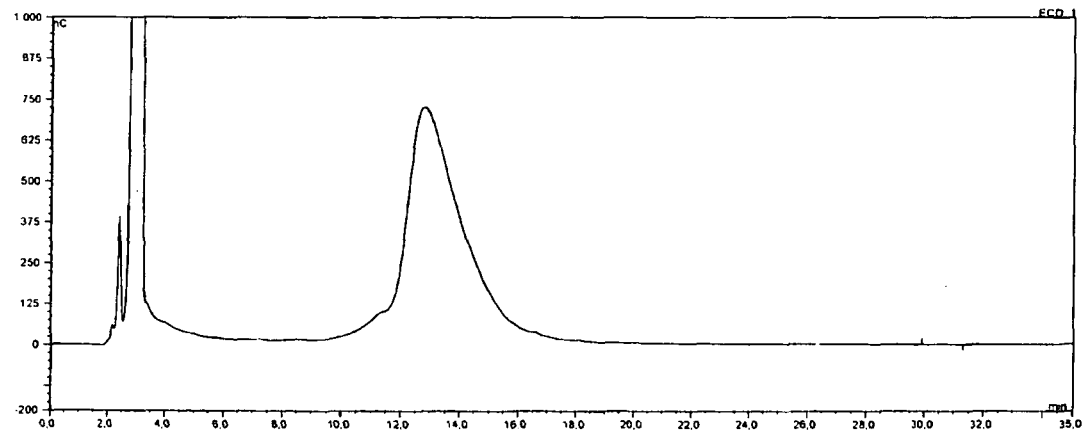

As shown in FIGS. 2 to 4, isocratic elution by sodium acetate 80 mM for 20 minutes can separate the hydrolyzed sucrose and the matrix impurities, and then gradient elution by sodium acetate from 80 mM to 300 mM (20-40 min) can separate mannosamine-6-phosphate.

Using spiking with known amounts of saccharide, the method was found to have an average recovery of about 95% for mannosamine-6-phosphate.

Validation

Having calibrated the separation method, it was used to test conjugate samples (CRM197 carrier) that had been lyophilized and stored for some time. Due to potential instability, these samples contained unknown amounts of unconjugated material (SL). Low and stable levels of unconjugated material during storage indicate stability.

The lyophilized samples were solubilised with 0.6 ml in $NaH_2PO_4.H_2O$ 5 mM+0.9% NaCl buffer, pH 7.2. Unconjugated and conjugated material in the ST samples were separated by extraction with a $CH_3CN$ 10%/0.05% TFA solution using no. 2 C4 100 mg 1 ml SPE columns. In three different lots the concentration or saccharide in the unconjugated fraction, determined by measuring the area of the relevant peak, was below the first point of the calibration standard curve i.e. less than 0.5 μg/ml Man-6-P. Thus the lyophilized materials are stable.

Combination Vaccines

The analytical method was also used to determine the amount of unconjugated MenA saccharide in a 4-valent mixture of CRM197-conjugated saccharides from meningococcal serogroups A, C, W135 and Y. Two different formulations of this 'MenACWY' vaccine were tested. Both formulations included 15 mg of sucrose per dose. The first sample had 61 g of MenA saccharide and 3 µg each of MenC, MenW and MenY; the second sample had double the MenACWY doses.

In all cases the method of the invention was able to detect total and unconjugated serogroup A saccharides. Spiking studies confirmed high recovery even in the presence of the other conjugates.

Figure 5A:
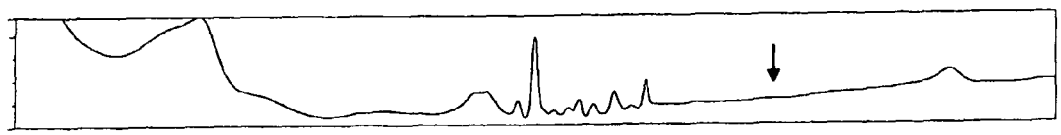
FIG. 5 shows a chromatogram of a MenACWY combination from 15-45 minutes elution. Three samples were tested: A, negative control; B, sample; C, spike sample. The arrow shows the position of the mannosamine-6-phosphate peak at around 37 minutes.
Figure 5B:
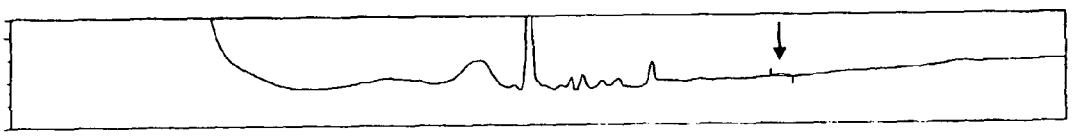
Figure 5C:

As an example, FIG. 5 shows results from three different samples: a negative control; a stored vaccine; and a stored vaccine spiked with a known amount of saccharide.

It will be understood that the invention has been described by way of example only and modifications may be made whilst remaining within the scope and spirit of the invention.

REFERENCES

The Contents of which are Hereby Incorporated in Full by Reference

[1] Ricci et al. (2001) *Vaccine* 19:1989-97.
[2] Gennaro (2000) *Remington. The Science and Practice of pharmacy.* 20th edition, ISBN: 0683306472.
[3] WO2005/090985
[4] Hardy et al. (1988) *Anal Biochem* 170:54-62.
[5] Wang et al. (1990) *Anal Biochem* 190:182-187.
[6] WO2005/114171.
[7] Berry et al. (2002) *Infect Immun* 70(7):3707-13.
[8] WO03/080678.
[9] Berkin et al. (2002) *Chemistry* 8(19):4424-33.
[10] Anonymous (January 2002) *Research Disclosure*, 453077.
[11] Anderson (1983) *Infect Immun* 39(1):233-238.
[12] Anderson et al. (1985) *J Clin Invest* 76(1):52-59.
[13] EP-A-0372501.
[14] EP-A-0378881.
[15] EP-A-0427347.
[16] WO93/17712
[17] WO94/03208.
[18] WO98/58668.
[19] EP-A-0471177.
[20] WO91/01146
[21] Falugi et al. (2001) *Eur J Immunol* 31:3816-3824.
[22] Baraldo et al. (2004) *Infect Immun* 72(8):4884-7.
[23] EP-A-0594610.
[24] Ruan et al. (1990) *J Immunol* 145:3379-3384.
[25] WO00/56360.
[26] Kuo et al. (1995) *Infect Immun* 63:2706-13.
[27] WO02/091998.
[28] WO01/72337
[29] WO00/61761.
[30] U.S. Pat. No. 4,761,283
[31] U.S. Pat. No. 4,356,170
[32] Porro et al. (1985) *Mol Immunol* 22:907-919.
[33] EP-A-0208375
[34] WO00/10599
[35] Gever et al. Med. Microbiol. Immunol, 165: 171-288 (1979).
[36] U.S. Pat. No. 4,057,685.
[37] U.S. Pat. Nos. 4,673,574; 4,761,283; 4,808,700.
[38] U.S. Pat. No. 4,459,286.
[39] U.S. Pat. No. 4,965,338
[40] U.S. Pat. No. 4,663,160.
[41] WO2007/000343.

The invention claimed is:

1. A method for assaying a sample suspected to contain a capsular saccharide from serogroup A *Neisseria meningitidis* ('MenA-CPS'), comprising the steps of: (i) hydrolysing any MenA-CPS in the sample, to give a hydrolysate; (ii) subjecting the hydrolysate to liquid chromatography; and (iii) detecting any mannosamine-6-phosphate separated in step (ii), wherein the sample in step (i) includes a lyophilisation stabilizer, wherein the lyophilization stabilizer is a saccharide, wherein the lyophilisation stabiliser and the MenA-CPS are not separated from each other prior to step (ii), and wherein step (ii) results in separation of the hydrolyzed capsular saccharide and the lyophilization stabilizer.

2. The method of claim 1, wherein the lyophilisation stabiliser is a disaccharide.

3. The method of claim 2, wherein the disaccharide is sucrose.

4. The method of claim 3, wherein sucrose is present in excess relative to MenA-CPS.

5. The method of claim 1, wherein the liquid chromatography is anion exchange chromatography.

6. The method of claim 1, wherein the sample contains unconjugated MenA-CPS and/or conjugated MenA-CPS.

7. The method of claim 6, wherein conjugated and unconjugated MenA-CPS in the sample are separated from each other prior to step (i).

8. The method of claim 7, wherein the separation uses solid phase extraction.

9. The method of claim 1, wherein step (ii) involves high performance anion exchange chromatography (HPAEC).

10. The method of claim 1, wherein step (iii) involves pulsed amperometric detection (PAD).

11. The method of claim 1, wherein step (ii) utilises a chromatography column comprising ethylvinylbenzene substrate crosslinked with divinylbenzene.

12. The method of claim 1, wherein step (i) involves acid hydrolysis.

13. The method of claim 1, wherein step (iii) is quantitative.

14. The method of claim 1, wherein the sample is prepared by separating conjugated and unconjugated MenA-CPS in a specimen, and then using the unconjugated material as the sample.

15. The method of claim 2, wherein the liquid chromatography is anion exchange chromatography.

16. The method of claim 2, wherein the sample contains unconjugated MenA-CPS and/or conjugated MenA-CPS.

17. The method of claim 16, wherein conjugated and unconjugated MenA-CPS in the sample are separated from each other prior to step (i).

18. The method of claim 17, wherein the separation uses solid phase extraction.

19. The method of claim 2, wherein step (ii) involves high performance anion exchange chromatography (HPAEC).

20. The method of claim 2, wherein step (iii) involves pulsed amperometric detection (PAD).

21. The method of claim 2, wherein step (ii) utilises a chromatography column comprising ethylvinylbenzene substrate crosslinked with divinylbenzene.

22. The method of claim 2, wherein step (i) involves acid hydrolysis.

23. The method of claim 2, wherein step (iii) is quantitative.

24. The method of claim 2, wherein the sample is prepared by separating conjugated and unconjugated MenA-CPS in a specimen, and then using the unconjugated material as the sample.

25. The method of claim 1, wherein the lyophilization stabilizer is present in milligram amounts and the MenA-CPS is present in microgram amounts.

\* \* \* \* \*